US011110117B2

(12) United States Patent
Lee et al.

(10) Patent No.: US 11,110,117 B2
(45) Date of Patent: Sep. 7, 2021

(54) SKIN PREPARATION COMPOSITION FOR EXTERNAL USE CONTAINING COMPLEX HYALURONIC ACID

(71) Applicants: J2KBIO CO., LTD., Cheongju-si (KR); COSMECCA KOREA CO., LTD., Chungcheongbuk-do (KR)

(72) Inventors: Jae Soeb Lee, Cheongju-si (KR); Jun Tae Bae, Cheongju-si (KR); Seok Jong Kim, Cheongju-si (KR); Young Kwon Cha, Yongin-si (KR); Hang Eui Cho, Yongin-si (KR); Ju Tae Jeong, Chungcheongbuk-do (KR); Kyeong Seok So, Yongin-si (KR)

(73) Assignees: J2KBIO CO., LTD., Cheongju-si (KR); COSMECCA KOREA CO., LTD., Chungcheonbuk-do (KR)

( * ) Notice: Subject to any disclaimer, the term of this patent is extended or adjusted under 35 U.S.C. 154(b) by 0 days.

(21) Appl. No.: 16/738,357

(22) Filed: Jan. 9, 2020

(65) Prior Publication Data

US 2021/0015847 A1    Jan. 21, 2021

(30) Foreign Application Priority Data

Jul. 17, 2019   (KR) ........................ 10-2019-0086168

(51) Int. Cl.
*A61K 31/728* (2006.01)
*A61P 17/04* (2006.01)
*A61Q 19/08* (2006.01)
*A61K 8/73* (2006.01)

(52) U.S. Cl.
CPC ............ *A61K 31/728* (2013.01); *A61K 8/735* (2013.01); *A61P 17/04* (2018.01); *A61Q 19/08* (2013.01)

(58) Field of Classification Search
CPC ........ A61K 31/728; A61K 8/735; A61P 17/04
USPC ......................................................... 514/54
See application file for complete search history.

(56) References Cited

U.S. PATENT DOCUMENTS 5,972,341 A    10/1999   Andre et al.

FOREIGN PATENT DOCUMENTS

| CN | 108478453 A | * | 9/2018 |
|---|---|---|---|
| JP | 64-85905 A | | 3/1989 |
| JP | 02-245087 A | | 9/1990 |
| JP | 03-294384 A | | 12/1991 |
| JP | 07-10769 A | | 1/1995 |
| JP | 09-67266 A | | 3/1997 |
| KR | 10-2004-0011584 A | | 2/2004 |
| KR | 10-0431076 B1 | | 5/2004 |
| KR | 10-0511494 B1 | | 8/2005 |
| KR | 10-0517465 B1 | | 9/2005 |
| KR | 1020080054627 A | | 6/2008 |
| KR | 10-2017-0117841 A | | 10/2017 |
| KR | 1020180138331 A | | 12/2018 |
| KR | 10-2019-0010795 A | | 1/2019 |
| KR | 10-1987559 B1 | | 6/2019 |

OTHER PUBLICATIONS

Xiao et al.; CN 108478453 A; Sep. 4, 2018 (Machine-English Translation).*
Barbara A. Gilchrest et al., "Skin aging and photoaging: An overview", Journal of the American Academy of Dermatology, Sep. 1989, pp. 610-613, vol. 21, No. 3, Part 2.
Irwin M. Braverman et al., "Studies in Cutaneous Aging: I. The Elastic Fiber Network", The Journal of Investigative Dermatology, 1982, pp. 434-443, vol. 78, No. 5.
Raphael Warren et al., "Age, sunlight, and facial skin: A histologic and quantitative study", Journal of the American Academy of Dermatology, Nov. 1991, pp. 751-760, vol. 25, No. 5, Part 1.

* cited by examiner

*Primary Examiner* — Shaojia A Jiang
*Assistant Examiner* — Michael C Henry
(74) *Attorney, Agent, or Firm* — Rabin & Berdo, P.C.

(57) ABSTRACT

Disclosed is a skin preparation composition for external use containing complex hyaluronic acid as an active ingredient, and specifically relates to a skin preparation composition for external use that contains hyaluronic acid, sodium hyaluronate, and hydrolyzed hyaluronic acid as active ingredients, and are excellent in an active oxygen scavenging effect, a wrinkle improvement effect, a moisturizing effect, a skin irritation relief effect, an acne prevention effect, an atopy improvement effect, and an anti-inflammatory effect, an hair damage prevention effect, and a hair loss prevention and hair growth effect.

4 Claims, No Drawings

SKIN PREPARATION COMPOSITION FOR EXTERNAL USE CONTAINING COMPLEX HYALURONIC ACID

BACKGROUND OF THE INVENTION

Field of the Invention

The present invention relates to a skin preparation composition for external use containing complex hyaluronic acid as an active ingredient, and specifically relates to a skin preparation composition for external use that contains hyaluronic acid, sodium hyaluronate, and hydrolyzed hyaluronic acid as active ingredients, and are excellent in an active oxygen scavenging effect, a wrinkle improvement effect, a moisturizing effect, a skin irritation relief effect, an acne prevention effect, an atopy improvement effect, and an anti-inflammatory effect, an hair damage prevention effect, and a hair loss prevention and hair growth effect.

Description of the Related Art

A skin aging can be divided into an intrinsic chronological and a photoaging [Gilchrest B A: J. Am. Acad. Dermatol., 21, 610-613 (1989)]. The intrinsic chronological is a naturally induced aging phenomenon that decreases the physiological function of the living body as the age increases [Braverman I M, etc.: J. Invest. Dermatol., 78, 434-443 (1982)]. The photoaging means that the skin is repeatedly exposed to light and the appearance or the function of the skin is changed [Ridder G M et al. J. Am. Acad. Dermatol., 25, 751-760 (1991)]. In addition, the skin aging can be caused by activation of reactive oxygen species due to UV rays, stress, disease conditions, environmental factors, wounds, and aging. If this condition deepens to destroy the antioxidant defenses existed in vivo and damage cells and tissues to promote adult disease and aging. More specifically, lipids, proteins, polysaccharides and nucleic acids, etc., which are the main components of the skin, are oxidized, so that the skin cells and the tissues are destroyed, and eventually skin aging phenomenon is generated. In particular, the oxidation of the protein cuts collagen, hyaluronic acid, elastin, proteoglycan, and fibronectin etc., which are the connective tissues of the skin, so that it causes a severe hyper-inflammatory response and interferes with the skin elasticity. If this phenomenon becomes more severe, it leads to a mutant phenomenon owing to DNA mutations, a cancer induction, and an immune function suppression.

Therefore, it eliminates the reactive oxygen species generated during the metabolic process of the body or the reactive oxygen species mediated by the ultraviolet irradiation and the inflammatory response to protect the cell membrane and already damaged cells are recycled by means of the active metabolism to multiply the cells, so that it can quickly recover the skin and maintain healthy skin. The aging involves not only the reactive oxygen species but also an enzyme called MMP. That is, the synthesis and decomposition of the extracellular matrix such as collagen in vivo are properly controlled. However, as the aging progresses, the synthesis thereof is reduced and the expression of matrix metalloproteinase, which is an enzyme of degrading the collagen, is promoted, so that the elasticity of the skin is reduced and the wrinkles are formed. In addition, these degradation enzymes are also activated by ultraviolet light. Therefore, the development of a material capable of controlling the expression of the MMP, in that the activation is induced in the cell by the ultraviolet light, or inhibiting its activity is required. Until now, most of the raw materials used as a material of cosmetics simply inhibit only the activity of the MMP enzyme.

Next, skin diseases mean the abnormality that appears on all the skin including hair, nails, and toenails of the mammals including people. An atopic dermatitis, that appears in people with atopic allergies, is a typical skin disease. The cause of the atopic dermatitis has not yet been clearly identified. However, there is a medical history of atopic dermatitis in about 70% of atopic dermatitis patients. Since it is easy to occur in people who are accompanied by other allergic diseases such as allergic rhinitis and asthma etc. in particular, it is understood as one of the genetic factors or the immune diseases. In case of the feature of the diseases, initially, severe itching causes most people to scratch the skin, thus causing secondary infections and especially it may worsen depending on the mental stability and emotional state of the patient. A lot of people surfer from the atopic dermatitis. 0.5-1% of the entire population and 5-10% of children surfer from it. Also, the symptoms usually appear within two to six months of age, especially in infants under one year of age, with 85% of patients occurring within five years of age. The atopic dermatitis is mainly occurred frequently in infancy, but in recent years, the number of patients after puberty has been increased and the medical history thereof is very long. In the treatment of the atopic dermatitis, drugs such as adrenocortical hormones etc. having high medicinal effect are used. However, the side effects of such adrenocortical hormones are problematic and the patients are exposed to the risk of side effects during the treatment period. Furthermore, it is also well known that the rebound (the disease aggravation of the affected area generated after the cessation of use of the drug) occurs by the cessation of use of the adrenocortical hormones. In order to overcome such side effects, non-steroidal anti-inflammatory or antihistamines that do not contain hormones such as adrenocortical hormones etc. are used. However, there is a problem in that it is hard to cure. Therefore, it is very urgent to reduce the atopic dermatitis or develop a therapeutic agent without the side effects.

Recently, a lot of attention has been focused on functional cosmetics with functions such as antioxidants, anti-wrinkle, whitening, itching relief obtained from natural extracts to reduce skin irritation due to a number of chemicals. The natural materials have fewer side effects on the skin and the positive response of the consumers to the cosmetics using the natural materials has increased recently. Accordingly, the development value of the cosmetics using the natural materials as a raw material is further increased. For example, U.S. Pat. No. 5,972,341 (Patent Literature 1) describes the wrinkle-improving effect on products extracted from a plant of the genus *Commiphora*, particularly the *Commiphora mukul* plant. Japanese Patent Publication No. H09-67266 describes a seaweed extract having hyaluronidase inhibitory efficacy. Japan Patent Publication No. H01-85905 describes the effect of improving the skin texture of fucoidan extracted from Wakame. Japan Patent Publication No. H02-245087 describes the antioxidant effect of the extract in Sargassum. Japan Patent Publication No. H03-294384 describes the antioxidant composition extracted from Hizikia. Japanese Patent publication No. H07-10769 describes a Phaeophyceae extract with an astringent effect. Korean Patent registration No. 10-0431076 (Patent Literature 2) discloses a cosmetic composition for improving the healing atopic dermatitis containing an extract of *Bletilla striata, Perilla ocymoides, Echinacea purpurea* and fermented soybean. Korean Patent registration No. 10-0511494 (Patent Literature 3) discloses extracts and compositions for the treatment of atopic dermatitis including fleeceflower, leaves of *Diospyros kaki*, and illite. Korea Patent publication No. 10-2004-0065126 (Patent Literature 4) discloses compositions of cosmetics for atopic skin containing oriental herbal extracts including extracts of Ling Chiu mushroom, *Ulmi* cortex, licorice, White *Poria cocos*, White *Sesamum indicum*, and *Opuntia ficus* etc. Also, Korea Patent publication No. 10-2004-0011584 (Patent Literature 5) discloses a herbal medicine composition for the atopic dermatitis and a manufacture method thereof by purifying natural products such as licorice roots, *Trigonella foenum-graecum* L., safflower, and pork fat and mixing them and having excellent therapeutic effect on atopic dermatitis.

In addition, since the androgenetic alopecia is dependent on androgen hormones, it is directly related to the amount of androgen. Accordingly, many studies have recently been reported for the prevention and treatment of hair loss through suppression of androgen activity. On the other hand, where the function of the sebaceous glands is elevated by the secretion rise of androgen hormones, a comedo generated when the excess sebum is stagnated in the hair follicles due to the hyperkeratosis of the hair follicle wall is an early stage of acne. When describing the mechanism of hair loss and acne caused by androgen hormones, 5α-Reductase is present in the male hormone reactive tissue such as sebaceous glands, hair follicles, prostate, epididymis etc. and is one of the androgen hormones. Also, it is an enzyme involved in metabolizing dihydrotestosterone with testosterone and the transition thereof requires NADPH. In addition, the testosterone is involved in male sexual impulses, skeletal muscle increase, male external genitalia, scrotum growth, sperm formation and the dihydrotestosterone is involved in the organizations related to acne, sebum increase, hair loss and benign prostatic hyperplasia etc. In particular, after puberty, excessive secretion of testosterone causes acne and hair loss. At this time, in order to prevent the excessive production of the dihydrotestosterone, which is the active form of androgen hormones, owing to the 5α-Reductase, researches on the development of anti-hair loss and anti-acne agents using 5α-Reductase inhibitors are actively conducted.

In order to solve these problems of the skin, recently, a lot of cosmetics using natural products have been developed to reduce skin irritation caused by a number of chemicals. Recently, since the natural materials have fewer side effects on the skin and the positive response of the consumers to the cosmetics using the natural materials has increased, the development value of the natural materials as a cosmetic raw material has increased. Thus, as a result of applying to cosmetics using hyaluronic acid having various molecular weights known so far by means of the present inventors, it can be found that a complex hyaluronic acid composite is excellent in comparison with a single molecular weight of hyaluronic acid in terms of an active oxygen scavenging effect, a wrinkle improvement effect, a moisturizing effect, a skin irritation relief effect, an acne prevention effect, an atopy improvement effect, and an anti-inflammatory effect, an hair damage prevention effect, and a hair loss prevention and hair growth effect, thereby expecting the effect as a cosmetic.

The hyaluronic acid is made of N-acetyl glucosamine and glucuronic acid. It is known that the hyaluronic acid is existed in the extracellular substrate, involved in moisture retention in the skin, cell growth factors, and storage and diffusion of nutrients, and synthesized by fibroblasts and keratinocytes. Also, it is known that this hyaluronic acid serves to prevent the moisture evaporation of the skin, serves as a thin and transparent moisturizing membrane, and penetrates deep into the skin from the external harmful environment.

PATENT LITERATURE

Patent Literature 1: U.S. Pat. No. 5,972,341 B (Oct. 26, 1999)
Patent Literature 2: KR 10-0431076 B (Apr. 29, 2004)
Patent Literature 3: KR 10-0511494 B (Aug. 24, 2005)
Patent Literature 4: KR 10-2004-0065126 A (Jul. 21, 2004)
Patent Literature 5: KR 10-2004-0011584 A (Feb. 5, 2004)

SUMMARY OF THE INVENTION

An object of the present invention is to use complex hyaluronic acid of hyaluronic acid (molecular weight; 2,000 kDa), sodium hyaluronate (molecular weight; 1,300 kDa) and hydrolyzed hyaluronic acid (molecular weight; 7 kDa) of different molecular weight sizes, to check the efficacy of the skin preparation for external use as a raw material, to develop the a method of using the same, and to provide a method of producing skin preparation for external use having excellent functionality by using the raw material.

That is, an object of the present invention is to provide a complex hyaluronic acid composition capable of being applied to a skin cosmetic and showing excellent anti-aging effects such as an active oxygen scavenging effect, a MMP-1 biosynthesis reduction, a type 1 procollagen biosynthesis promoting effect, a skin wrinkle improvement effect, an anti-inflammatory effect etc. during containing in the cosmetic.

In addition, an object of the present invention is to provide a complex hyaluronic acid composition showing a skin irritation relief effect by the inflammatory mediator when it is applied to the skin cosmetic.

In addition, an object of the present invention is to provide a complex hyaluronic acid composition showing a moisturizing effect and an atopy improvement effect when it is applied to the skin cosmetic.

In addition, an object of the present invention is to provide a complex hyaluronic acid composition showing an excellent hair damage prevention effect, a hair loss prevention, hair growth effect and an acne prevention effect.

In addition, an object of the present invention is to provide a method for preparing a cosmetic using a complex hyaluronic acid composition, and a cosmetic thereof.

According to an aspect of the invention to achieve the object described above, there is provided a skin preparation composition for external use containing complex hyaluronic acid, wherein complex hyaluronic acid obtained by mixing hyaluronic acid, sodium hyaluronate, and hydrolyzed hyaluronic acid is contained by 0.001 to 3 weight % with respect to the total composition.

In the above composition, the skin preparation composition for external use has an anti-aging effect.

Also, the skin preparation composition for external use has an irritation relief function.

In addition, the skin preparation composition for external use has an atopic skin improvement function.

Moreover, the skin preparation composition for external use has an irritation relief function.

DETAILED DESCRIPTION OF THE PREFERRED EMBODIMENT

In order to achieve the above objects, the present invention is to provide a skin preparation composition for external use containing complex hyaluronic acid (referred to as 'complex hyaluronic acid'), wherein complex hyaluronic acid obtained by mixing hyaluronic acid, sodium hyaluronate, and hydrolyzed hyaluronic acid is contained by 0.001 to 3 weight % with respect to the total composition.

The complex hyaluronic acid refers to a composition obtained by mixing and dispersing hyaluronic acid (molecular weight; 2,000 kDa), sodium hyaluronate (molecular weight; 1,300 kDa), and hydrolyzed hyaluronic acid (molecular weight; 7 kDa) which have different molecular weight in purified water.

The composition of the complex hyaluronic acid may be 0.05 to 2.0 weight % of hyaluronic acid, 0.05 to 2.0 weight % of sodium hyaluronate, 0.05 to 2.0 weight % of hydrolyzed hyaluronic acid, and the remaining amount of purified water.

When the content of the complex hyaluronic acid in the skin preparation composition for external use is less than 0.001 weight %, the skin preparation composition has very few skin improvement effects. When the content is 3.0 weight % or more, the amount of the increase of the effect with respect to the increase of the content is very insignificant, and thus it is not economical.

The present invention provides a skin preparation composition for external use that contains complex hyaluronic acid in which the skin preparation composition for external use has a formulation selected from a toner, a gel, a water-soluble liquid, cream, an essence, an oil-in-water (O/W) type, and a water-in-oil (W/O) type.

According to the present invention, the skin external preparation is a cosmetic composition or a pharmaceutical composition.

The complex hyaluronic acid can be formulated as a pharmaceutical composition such as a capsule, a liquid, an ointment, a patch, and a sustained release agent using a pharmaceutically acceptable carrier, and includes a pharmacologically acceptable base, a carrier, an excipient, a binder, (for example: starch, tragacanth rubber, gelatin, molasses, polyvinyl alcohol, polyvinyl ether, polyvinyl pyrrolidone, hydroxypropyl cellulose, methyl cellulose, ethyl cellulose, and carboxymethyl cellulose), a pulverized agent (for example: agar, starch, bellatin powder, carboxymethyl cellulose sodium, carboxymethyl cellulose calcium, crystalline cellulose, calcium carbonate, sodium hydrogen carbonate, and sodium alginate), a lubricating agent (for example: magnesium stearate, talc, and hydrogenated vegetable oil), and a coloring agent. As the carrier or the excipient, lactose, glucose, sucrose, mannitol, potato starch, corn starch, calcium carbonate, calcium phosphate, cellulose, and the like are used.

In addition to the above, an aid such as a stabilizer, a solubilizer, and a transdermal absorption accelerator, and an additive such as a flavoring agent and a preservative may be further added.

The pharmaceutical composition produced in this manner can be applied to skin once or several times a day depending on the symptoms, and the application can be adjusted depending on the improvement of symptoms.

Hereinafter, the present invention is more specifically described with reference to examples and experiment examples. Here, the examples only illustrative examples of the present invention, and the scope of the present invention is not limited to these examples.

Example 1: Production of Complex Hyaluronic Acid

As hyaluronic acid powder having different molecular weights, 0.2 g (0.05 weight %) of hyaluronic acid (molecular weight; 2,000 kDa), 0.2 g (0.05 weight %) of sodium hyaluronate (molecular weight; 1,300 kDa), and 5 g (1.25 weight %) of hydrolyzed hyaluronic acid (molecular weight; 7 kDa) were mixed in 394.6 g of purified water, to produce complex hyaluronic acid.

Experiment Example 1: Experiment of Measuring Antioxidant Effect Using NBT Method In order to check an antioxidant effect of the complex hyaluronic acid obtained in Example 1, by using monomolecular hyaluronic acid and butylated hydroxytoluene (BHT), which is well-known as an antioxidant, as comparison samples, antioxidant activity was measured by a nitro blue tetrazolium (NBT) method in a laboratory condition.

In order to measure the antioxidant effect, active oxygen generated by xanthine and xanthine oxidase was measured by the NBT method, and an effect of removing active oxygen by a test substance, that is, the active oxygen scavenging effect was evaluated.

Active oxygen was generated by xanthine and xanthine oxidase, and this active oxygen reacts with nitro blue tetrazolium (NBT). A blue color generated by this reaction was measured in a wavelength of 560 nm, to measure an active oxygen scavenging rate.

As the measuring method, 2.4 ml of 0.05 M Na2CO3, 0.1 ml of a 3 mM xanthine solution, 0.1 ml of a 3 mM EDTA solution, 0.1 ml of a BSA solution, and 0.1 ml of a 0.72 mM NBT solution were added to a Bayer bottle, 0.1 ml of each sample solution was added thereto, and the resultant was left for 10 minutes at 25° C.

0.1 ml of a xanthine oxidase solution was added and quickly stirred, culture at 25° C. for 20 minutes was started, 0.1 ml of a 6 mM $CuCl_2$ solution was added to stop the reaction, and an absorbance St at 560 nm was measured.

In a blank test, the same operation was performed in the same manner except that distilled water was used instead of the sample solution, and an absorbance Bt was measured. In a blank of the sample solution, the same operation was performed in the same manner except that the distilled water was used instead of xanthine oxidase, and an absorbance Bo was measured.

The effect was calculated by Equation 1, and results thereof are shown in Table 1.

Inhibition rate (%)=$[1-(St-So)/(Bt-Bo)] \times 100$     <Equation 1>

St: Absorbance at 560 nm after enzyme reaction of sample solution

Bt: Absorbance at 560 nm after enzyme reaction of blank test solution

So: Absorbance at 560 nm before reaction of sample solution in the absence of enzyme Bo: Absorbance at 560 nm before reaction of blank test solution in the absence of enzyme

TABLE 1

| Name of sample | Intracellular antioxidant effect (%) |
| --- | --- |
| Example 1, 0.1 weight % | 89% |
| Hyaluronic acid (2,000 kDa), 0.1 weight % | 72% |
| Sodium hyaluronate (1,300 kDa), 0.1 weight % | 70% |

TABLE 1-continued

| Name of sample | Intracellular antioxidant effect (%) |
|---|---|
| Hydrolyzed hyaluronic acid (7 kDa), 0.1 weight % | 23% |
| BHT, 0.1 weight % | 87% |

As can be seen from Table 1 above, the complex hyaluronic acid had more excellent antioxidant capacity than the monomolecular hyaluronic acid, and had antioxidant capacity similar to that of BHT.

Experiment Example 2: Experiment of Measuring Free Radical Scavenging Activity

In order to measure free radical scavenging activity of the complex hyaluronic acid obtained in Example 1, by using monomolecular hyaluronic acid and an antioxidant such as BHT as comparison samples, free radical scavenging activity was measured by a DPPH method in a laboratory condition.

In the DPPH method, a free group called DPPH (2,2-di(4-tert-octylphenyl)-1-picrylhydrazyl free radical) is used so as to measure free radical scavenging activity by reducing force, a degree of decrease in absorbance due to the reduction of DPPH by a test substance was compared with the absorbance in the blank test solution to measure a free radical scavenging rate at a wavelength of 560 nm.

Each sample was prepared at the concentration of 0.1% to measure DPPH free radical scavenging activity. Each sample at the above concentration was introduced to a 96-well plate, and DPPH produced with a 100 uM methanol solution was added thereto, such that the total volume of the solution became 200 µl. The resultant was left for 30 minutes at 37° C., and an absorbance was measured at 560 nm. The free radical scavenging activity (%) was calculated by Equation 2 below.

Free radical scavenging activity (%)=100−($B/A$)×100  <Equation 2>

A: Absorbance of control wells in the absence of sample treatment

B: Absorbance of experimental wells with sample treatment

The free radical scavenging activity calculated in Equation 2 is shown in Table 2 below.

TABLE 2

| Name of sample | Free radical scavenging activity (%) |
|---|---|
| Example 1, 0.1 weight % | 85.2% |
| Hyaluronic acid (2,000 kDa), 0.1 weight % | 75.4% |
| Sodium hyaluronate (1,300 kDa), 0.1 weight % | 78.6% |
| Hydrolyzed hyaluronic acid (7 kDa), 0.1 weight % | 34.7% |
| BHT, 0.1 weight % | 81% |

As can be seen from Table 2, the complex hyaluronic acid had more excellent free radical scavenging activity than the monomolecular hyaluronic acid and BHT.

Experiment Example 3: Intracellular Active Oxygen Scavenging Effect

In order to confirm the effect of inhibiting the generation of active oxygen generated in the cell caused by the ultraviolet rays by the complex hyaluronic acid obtained in Example 1, that is, the active oxygen scavenging effect, monomolecular hyaluronic acid and EGCG were used as comparative samples, and the following experiment was performed by using a fluorescent material.

Cell lines used in the experiment were the Human keratinocytes HaCaT cell lines distributed from Dr. Fusenig in German Cancer Research Center. These cell lines were inoculated into a 96-well black plate for fluorescence measurement by $2.0 \times 10^4$ for each well and cultured for one day in the conditions of 37° C. and 5% CO2 by using a medium of Dulbecco's Modification of Eagle's Medium (DMEM, FBS 10%, Gibco, USA) with penicillin/streptomycin added, and the samples were treated at the concentration of 0.01%.

The test sample was introduced and cultured for 24 hours and washed with a HEPES-buffered control salt solution (HCSS) to remove the remaining medium, and 100 µl of 2',7'-dichlorodihydro-fluorescein diacetate (DCFH-DA, Molecular Probes, USA) prepared at 20 µM was added to HCSS, was cultured in the conditions of 37° C., 5% CO2 for 20 minutes, and washed with HCSS. Subsequently, 100 µl of HCSS treated for each concentration was added, and then the fluorescence of dichlorofluorescein (DCF) oxidized with active oxygen in the early stage was measured with a fluorescent plate reader (Ex; 485 nm, and Em; 530 nm). Subsequently, irradiation with UVB (20 mJ/cm$^2$) was performed, and the fluorescence after the sample treatment was measured by a fluorescent plate reader (Ex; 485 nm, and Em; 530 nm).

As can be seen from Table 3, it was understood that the complex hyaluronic acid has an excellent active oxygen scavenging effect similar to that of EGCG, which is widely used as a comparative sample for the active oxygen scavenging effect.

TABLE 3

| Name of sample | Active oxygen scavenging effect (%) |
|---|---|
| Example 1, 0.01 weight % | 46 |
| Hyaluronic acid (2,000 kDa), 0.01 weight % | 42 |
| Sodium hyaluronate (1,300 kDa), 0.01 weight % | 38 |
| Hydrolyzed hyaluronic acid (7 kDa), 0.01 weight % | 27 |
| EGCG 0.01 weight % | 45 |

Experiment Example 4: Experiment of In Vitro MMP-1 Activity Inhibition

In order to measure an MMP-1 activity inhibition effect, fluorescence analysis was used. A substrate used in the experiment was DQ-Collagen labeled with a fluorescent substance. As an enzyme (collagenase), a product commercially available from Molecular probe (Eugene, Oreg., USA) was used, and a reaction buffer solution (0.5 M Tris-HCl, 1.5 M NaCl, 50 mM CaCl$_2$), 2 mM sodium azide, pH 7.6) was used after 10 times dilution. 20 µl of DQ collagen dissolved in the reaction buffer solution at 0.25 mg/Ml and 40 µl of the sample (0.02 wt %) were added to 100 µl of the reaction buffer solution, and 40 µl of collagenase diluted to 0.5 units was added thereto. After 20 minutes at room temperature in the dark, a fluorescence value was measured at an absorption wavelength of 495 nm and an emission wavelength of 515 nm by using a fluorescence spectrophotometer (PerkinElmer Inc., UK). As a control, instead of enzyme, the same amount of the reaction buffer solution was added, and the fluorescence values was measured. The fluorescence value of the sample itself was also measured and the calculation of enzyme activity was corrected.

The results are shown in Table 4, and when 0.02% of complex hyaluronic acid was treated, 79% of the collagen degrading activity of clostridial collagenase was inhibited. This inhibition was more excellent than the inhibition effect of green tea extract.

TABLE 4

| Name of sample | Inhibition rate (%) |
|---|---|
| Example 1, 0.02 weight % | 79 |
| Hyaluronic acid (2,000 kDa), 0.02 weight % | 64 |
| Sodium hyaluronate (1,300 kDa), 0.02 weight % | 58 |
| Hydrolyzed hyaluronic acid (7 kDa), 0.02 weight % | 21 |
| Green tea extract 0.02 weight % | 72 |

Experiment Example 5: Evaluation of MMP-1 Expression Inhibition by Complex Hyaluronic Acid after Ultraviolet Irradiation In this experiment example, in order to measure the MMP-1 concentration after UV irradiation and sample addition of the complex hyaluronic acid obtained in Example 1, enzyme-linked immunosorbent assay (ELISA) was performed.

Human dermal fibroblasts were irradiated with UVA at an energy of 6.3 J/cm$^2$ by using a UV chamber. With respect to UV irradiation dose and culture time, conditions for maximizing an MMP expression amount in fibroblasts were established by preliminary experiments. A negative control was wrapped in silver foil and kept for the same period of time in the UVA environment. A UVA emission amount was measured by using a UV radiometer. The cells during the UVA irradiation were the same medium inoculated before without change and were exchanged with a medium containing the samples after UVA irradiation. The medium was collected after culturing for 24 hours, and 96 wells were coated with the medium. A primary antibody (MMP-1 (Ab-5) monoclonal antibody) was treated and reacted at 37° C. for 60 minutes. After an anti-mouse IgG (whole mouse, alkaline phosphatase conjugated), which was a secondary antibody, was reacted again for about 60 minutes, the alkaline phosphatase substrate solution (1 mg/ml p-nitrophenyl phosphate in diethanolamine buffer solution) was reacted at room temperature for 30 minutes, and then an absorbance was measured at 405 nm with a plate reader. As a control, a medium to which the sample was not added was used.

In MMP-1 of which the expression was induced during UV irradiation, compared to the control in which the sample was not treated, complex hyaluronic acid showed an inhibition rate of 37% or more, and this was an inhibition rate similar to that of retinol used as a control.

TABLE 5

| Experimental group | MMP-1 expression inhibition rate (%) |
|---|---|
| Control | — |
| Example 1, 0.02 weight % | 37 |
| Hyaluronic acid (2,000 kDa), 0.02 weight % | 30 |
| Sodium hyaluronate (1,300 kDa), 0.02 weight % | 28.1 |
| Hydrolyzed hyaluronic acid (7 kDa), 0.02 weight % | 15 |
| Retinol | 38 |

Experiment Example 6: Type 1 Procollagen Biosynthesis Promoting Effect

In this experiment example, in order to confirm an effect of promoting the biosynthesis of type 1 procollagen, which was a skin substrate ingredient, after the addition of complex hyaluronic acid obtained in Example 1, the procollagen assay was performed in the following method.

Human dermal fibroblasts isolated from neonatal foreskin tissues were distributed from Modern Tissue Technology (MTT, Korea), and a 10% fetal bovine serum (FBS) was added to a medium of DMEM/F-12 (3:1) and cultured at the concentration of $1\times10^4$ cell/cm$^2$. At about 70% to 80% confluence, the cells were inoculated at a ratio of 1:3 and subcultured, and the cells subcultured for the third to fourth generations were used in the experiment.

For experiments to measure the amount of procollagen, the fibroblasts were cultured by more than 90% in a 48-well plate, and then each of complex hyaluronic acid and monomolecular hyaluronic acid was added at the concentration of 0.02%, and an amount of collagen isolated in the medium after 24 hours was measured by using a procollagen type-1 C-peptide EIA kit (MK101, Takara, Japan).

The results are shown in Table 6, and when 0.02% of complex hyaluronic acid was treated, biosynthesis of the procollagen was promoted by 30%, and this shows the same effect as TGF-8, which is was a cell signaling material.

TABLE 6

| Name of sample | Procollagen biosynthesis promoting effect (%) |
|---|---|
| Example 1, 0.02 weight % | 30% |
| Hyaluronic acid (2,000 kDa), 0.02 weight % | 14% |
| Sodium hyaluronate (1,300 kDa), 0.02 weight % | 11.1% |
| Hydrolyzed hyaluronic acid (7 kDa), 0.02 weight % | — |
| TGF-β 0.001 weight % | 35% |

Experiment Example 7: Elastin Production Promoting Effect of Complex Hyaluronic Acid In order to search the elastin production promoting effect of the complex hyaluronic acid and an effect of inhibiting the elastase activity, the complex hyaluronic acid of Example 1 was treated on fibroblasts of humans directly collected from humans or commercially purchased, and the following experiment was performed.

First, human fibroblasts were introduced into a culture flask and cultured to reach about 70% to 80% confluence.

Subsequently, after a treatment with the complex hyaluronic acid for one day, the cell culture medium was collected, and a degree of elastin production was measured by using a commercially available elastin measuring instrument [Bieth J: Biochem med., 11, 350-357 (1974), Schwartz D E: J. Invest Dermatol., 86, 63-68 (1986)]. That is, Suc-(Ala) 3 NA which is a substrate of elastase was used, the color change which arises when NA decomposes was measured by using the absorbance, and the activity of elastase was measured. At this time, a group without treatment with complex hyaluronic acid was used as a control.

As shown in Table 7, it can be understood that the complex hyaluronic acid inhibits the activity of elastase more prominently than the control, and it was checked that the activity inhibition rate increased as the concentration of the complex hyaluronic acid increased. Accordingly, it can be understood that, the complex hyaluronic acid exhibits excellent anti-aging and elasticity promoting effects.

TABLE 7

| Name of sample | Material activity inhibition rate (%) |
| --- | --- |
| Example 1, 0.02 weight % | 26% |
| Example 1, 0.01 weight % | 17% |
| Example 1, 0.005 weight % | 7.8% |
| Control | 0% |

Experiment Example 8: Effect of Relieving Cytotoxicity by UV Irradiation

This experiment example was performed to evaluate the effect of relieving cytotoxicity by ultraviolet irradiation by the complex hyaluronic acid obtained in Example 1. $1 \times 10^5$ of fibroblasts each were placed in a 24-well experimental plate and allowed to attach for 24 hours. Each well was washed once with PBS, and 500 ul of PBS was added to each well. After these fibroblasts were irradiated with 10 mJ/cm$^2$ of ultraviolet rays by using an ultraviolet B (UVB) lamp (Model: F15T8, UV B 15W, Sankyo Denki Co., Ltd., Japan), the PBS was removed, and 1 ml of a cell culture medium (10% FBS added to DMEM) was added. This was treated with the complex hyaluronic acid to be evaluated, and cultured for 24 hours. After 24 hours, the medium was removed, and 500 µl of the cell culture medium and 60 µl of the MTT solution (2.5 mg/ml) were introduced into each well, and then cultured in a CO2 incubator at 37° C. for two hours. The medium was removed and 500 µl of isopropanol-HCl (0.04 N) each was added. After shaking for five minutes, the cells were lysed and 100 µl of a supernatant each was transferred to a 96-well test plate, and then an absorbance at 565 nm was measured using a microplate reader. A cell survival rate (%) was measured by Equation 3, a rate of relieving cytotoxicity caused by ultraviolet rays was calculated by Equation 4.

Cell survival rate (%)=[(St−Bo)/(Bt−Bo)]×100     <Equation 3>

Bo: Absorbance at 565 nm of wells in which color reaction was performed only in cell culture medium Bt: Absorbance at 565 nm of wells in which color reaction was performed in wells without sample treatment St: Absorbance at 565 nm of wells in which color reaction was performed in wells with sample treatment Rate of relieving cytotoxicity caused by ultraviolet rays (%)=[1−(St−Bo)/(Bt−Bo)]×100     <Equation 4>

Bo: Cell survival rate of wells without ultraviolet irradiation nor sample treatment Bt: Cell survival rate of wells irradiated with ultraviolet without sample treatment St: Cell survival rate of wells irradiated with ultraviolet and treated with sample The calculation results are shown in Table 8 below.

TABLE 8

| Name of sample | Treatment Concentration (%) | Cytotoxicity relieving rate (%) |
| --- | --- | --- |
| Example 1 | 0.02 | 30.6 |
|  | 0.01 | 19.5 |
|  | 0.005 | 8.4 |

As shown in Table 8, as a result of the experiment, it was understood that the complex hyaluronic acid relieved cytotoxicity caused by the ultraviolet rays by 30.6% at the concentration of 0.02% and effectively protected the cytotoxicity caused by the ultraviolet rays.

That is, from the above experiment, it can be understood that the cell damage by ultraviolet rays is effectively protected at a low concentration.

Experiment Example 9: Effect of Inhibiting Inflammatory Cytokine Expression Caused by Ultraviolet Irradiation In this experiment example, in order to evaluate the effect of inhibiting the inflammatory cytokine expression expressed by UV irradiation of the complex hyaluronic acid obtained in Example 1, $5 \times 10^4$ of fibroblasts isolated from human epidermal tissues each were introduced in a 24-well experimental plate and allowed to be attached for 24 hours. Each well was washed once with PBS, and 500 µl of PBS was added to each well. After these fibroblasts were irradiated with 10 mJ/cm$^2$ of ultraviolet rays by using an ultraviolet B (UVB) lamp (Model: F15T8, UV B 15W, Sankyo Denki Co., Ltd., Japan), the PBS was removed, and 350 ml of a cell culture medium (a medium obtained by not adding FBS to DMEM) was added. This was treated with the complex hyaluronic acid to be evaluated, and cultured for 5 hours. 150 µl of the culture supernatant was taken and IL-1a was quantified, to determine the effect of inhibiting the inflammatory cytokine expression by the complex hyaluronic acid. The amount of IL-1a was quantified using enzyme-linked immunosorbent assay, and the production rate of IL-1a was calculated by Equation 5.

Rate of inhibiting the inflammatory cytokine expression (%)=[1−(St−Bo)/(Bt−Bo)]×100     <Equation 5>

Bo: Production amount of IL-1a in wells without ultraviolet irradiation nor sample treatment Bt: Production amount of IL-1a in wells irradiated with ultraviolet without sample treatment St: Production amount of IL-1a in wells irradiated with ultraviolet and treated with sample Experimental results according to Equation 5 are shown in Table 9 below.

TABLE 9

| Name of sample | Treatment Concentration (%) | Rate of inhibiting the inflammatory cytokine expression (%) |
| --- | --- | --- |
| Example 1 | 0.02 | 27 |
| | 0.01 | 15.2 |
| | 0.005 | 10.5 |

As shown in Table 9, it can be seen that the complex hyaluronic acid inhibits the generation of IL-1a, which is inflammatory cytokine, expression caused by ultraviolet rays at a concentration of 0.02% by 27%, and effectively protects the occurrence of inflammation caused by ultraviolet rays at a low concentration.

Experiment Example 10: Effect of Inhibiting Prostaglandin Biosynthesis Caused by Ultraviolet Irradiation In this experiment example, in order to evaluate the effect of inhibiting prostaglandin biosynthesis of the complex hyaluronic acid obtained in Example 1, $5\times10^4$ of keratinocytes isolated from human epidermal tissues each were introduced into a 24-well test plate and were allowed to be attached for 24 hours. The medium was replaced with a medium without FBS and was cultured for 18 hours, and then the keratinocytes were treated with aspirin such that the final concentration became 50 uM to remove the activity of prostaglandin synthetase (prostaglandin E2 synthetase or cyclooxygenase, hereinafter, referred to as COX) present in the keratinocytes. After two hours from the aspirin treatment, each well containing keratinocytes was washed twice with PBS, and 100 µl of PBS was added to each well. After these keratinocytes were irradiated with 30 mJ/cm$^2$ of ultraviolet rays by using a UVB lamp (Model: F15T8, UV B 15W, Sankyo Denki Co., Ltd., Japan), the PBS was removed, and 250 µl of keratinocyte growth media (Clonetics, Biowhittacker, Inc., MD, USA) was added to each well. This was treated with the complex hyaluronic acid to be evaluated, and cultured for 16 hours. An appropriate amount of the culture supernatant was taken, and prostaglandin E2 (PGE2) biosynthesized for 16 hours was quantified to determine the effect of inhibiting prostaglandin by the complex hyaluronic acid. The amount of PGE2 was quantified by using enzyme immunoassay, and results of the experiment are shown in Table 10 below.

TABLE 10

| Name of sample | PGE$_2$ inhibition rate (%) |
| --- | --- |
| (−) UV B | control |
| (+) UV B | — |
| (+) UV B + Example 1 0.02 weight % | 34% |
| (+) UV B + Example 1 0.01 weight % | 21% |
| (+) UV B + Example 1 0.005 weight % | 9.5% |

As shown in Table 10 above, it was understood that the complex hyaluronic acid effectively inhibited the production of prostaglandins by ultraviolet rays. In particular, since produced PGE2 is known to be produced mainly by the COX-2 enzyme, it can be seen from the above experiment that the complex hyaluronic acid inhibits the induction effect or activity of the COX-2 enzyme.

Experiment Example 11: Experiment of Evaluating 5-Alpha-Reductase Activity Inhibition Force of Complex Hyaluronic Acid As 5-alpha-reductase used in an experiment of inhibiting 5-alpha-reductase activity force of complex hyaluronic acid, enzymes produced by foreskin-derived fibroblasts were used.

Fibroblasts were seeded such that $1\times10^4$ cells were introduced for each microplate hole, and cultured. Testosterone radiolabeled with $^3$H (tritium) was added to each hole by 0.1 mp·Ci and cultured, and measurement on whether the fibroblasts used this is performed. A group in which hyaluronic acid is not included is used as a control. After 24 hours of incubation, the supernatant was obtained, and steroids were obtained with 1 ml of an ethyl acetate-cyclohexane (1:1) extraction solvent. The obtained steroid was placed on a thin layer chromatography plate and developed with a chloroform/methanol mixture liquid (98/2 (v/v)). The radioactivity at the points corresponding to testosterone and dihydrotestosterone was measured using a densitometer to calculate a conversion rate, and the result was compared with the control (conversion rate without addition of the extract), to evaluate 5-alpha-reductase inhibition force by Equation 6.

Inhibition force evaluation method Inhibition force (%)=[$A-B$]/[$A$]×100        <Equation 6>

A=Conversion rate of testosterone to dihydrotestosterone (without addition of extract)

B=Conversion rate of testosterone to dihydrotestosterone (with addition of extract)

Calculation results by Equation 6 are shown in Table 11 below.

TABLE 11

| | Example 1 Concentration (%) | | |
| --- | --- | --- | --- |
| | 0.02 | 0.01 | 0.005 |
| Inhibition rate (%) | 32.5 | 14.7 | 9.1 |

As can be seen in Table 11, it can be understood that the complex hyaluronic acid has an effect of inhibiting 5-alpha-reductase.

Experiment Example 12: Anti-Inflammatory Experiment of Complex Hyaluronic Acid after Atopic Dermatitis Induction by Compound 48/80

30 µl of Compound 48/80 (Sigma, Co.; 1 mg/ml in saline) for each mouse were injected into the dermis of the dorsal neck skin of BALB/c mice (5 wks, male). The mice were introduced into a cage and behaviors of the mice scratching on the neck was observed for 60 minutes. In order to test the anti-inflammatory effect of the complex hyaluronic acid, from five days before Compound 48/80 injection, the complex hyaluronic acid at a concentration of 250 µl/ml was applied to the dorsal necks of the mice by 100 µl of for each mouse. In the application method, the application was performed on the dorsal neck area of the mouse twice a day for five days, for 10 times in total for a pre-treatment, Compound 48/80 was then injected, and the amount of time the mouse scratching on the neck with the back foot is measured at intervals of 5 minutes for a total of one hour to measure a degree of the pruritus.

The experiment results are shown in Table 12.

TABLE 12

| | Number of scratching (in 5 min) | | | | | | | | | | | |
|---|---|---|---|---|---|---|---|---|---|---|---|---|
| | 5 | 10 | 15 | 20 | 25 | 30 | 35 | 40 | 45 | 50 | 55 | 60 |
| Example 1 | 29 | 34 | 34 | 34 | 32 | 33 | 39 | 40 | 42 | 36 | 29 | 25 |
| Control | 37 | 48 | 49 | 60 | 82 | 95 | 94 | 78 | 56 | 47 | 39 | 35 |

As shown in Table 12, when the complex hyaluronic acid was used, an effect of inhibiting the induction of atopic dermatitis (skin pruritus) caused by Compound 48/80 was exhibited.

Experiment Example 13: Experiment of Moisture Hygroscopicity

In order to perform experiment on the moisture hygroscopicity of complex hyaluronic acid, dry human epidermal cells directly collected from humans or commercially purchased are caused to absorb the complex hyaluronic acid of Example 1 and distilled water to be saturated, the amount of water absorbed was measured, and then the mass change after 48 hours drying was measured. The amount of absorbed water per unit mass of skin cells was compared with each measured change in mass. This experiment is a method of comparing the amount of water absorbed by epidermal cells and is used as one of the ways for estimating the moisturizing effect in the skin of real humans.

Specifically, after the human epidermal cells were dried to cause an amount of water contained per unit mass to be constant, the weight of each epidermal cell sample and the amount of contained water therein were measured using the Kaiser method. The epidermal cells in which the content of water was measured were immersed in complex hyaluronic acid (A) and purified water (B) for 24 hours for saturation absorption, epidermal cells in which water was saturated and absorbed in the cells were weighed, some were collected, and the amount of water per unit mass was measured by a Kaiser moisture meter. After 48 hours of reduced pressure drying and weighing, some were collected, and the water content was measured by a Kaiser method to measure the amount of contained water per unit mass.

As a result of the experiment, water supply capacities (moisture mg/epidermal cell mass g) for epidermal cells are shown in Table 13.

TABLE 13

| | Water content | | |
|---|---|---|---|
| | Initial dry state | Saturated state | After drying |
| Example 1 + Purified Water | 400 | 810 | 560 |
| Purified Water | 400 | 770 | 400 |

As shown in Table 13, it was confirmed that the epidermal cells saturated and absorbed with complex hyaluronic acid contained much more water than the epidermal cells saturated and absorbed with the purified water in the process of redrying epidermal cells saturated and absorbed with the purified water, and thus excellent skin hygroscopicity of the complex hyaluronic acid was able to be confirmed. According to this, it can be understood that the complex hyaluronic acid exhibits an excellent moisturizing effect.

Experiment Example 14: Effect of Binding Complex Hyaluronic Acid and Human Hair Protein Complex hyaluronic acid was added to 50 μg of human hair keratin protein at test concentrations of 0.02, 0.01, and 0.005 weight %, respectively, reaction was performed at room temperature for 30 minutes, a treatment was performed with a 1:1 mixed solution of 6% hydrogen peroxide and 0.5% ammonia, and reaction was performed for 30 minutes. The reaction solution was electrophoresed on a 10% SDS-polyacrylamide gel by the method of Laemmli, and the keratin protein in the gel was dyed for one hour with a mixed solution of 0.1% of Coomassie brilliant blue R 250, 10% of glacial acetic acid, and 40% of ethanol and was bleached in a mixed solution of 10% of glacial acetic acid and 40% of ethanol, to check a keratin protein band. A keratin band seen when only 50 μg of human hair keratin protein was electrophoresed by using ImageMaster software (Amersham Pharmacia Biotech.) was set to 100%, comparison was performed with the group without the complex hyaluronic acid treatment as a control, and a keratin bonding effect was shown in Table 14 below in terms of %.

TABLE 14

| | | Example 1 | | |
|---|---|---|---|---|
| | Control | 0.02% | 0.01% | 0.005% |
| Effect of binding hair protein | 0 | 72% | 47% | 31% |

As shown in Table 14, it can be understood that as the complex hyaluronic acid content increases, the binding capacity with the hair protein keratin increases.

Experiment Example 15: Protective Effect of Complex Hyaluronic Acid on Keratin Elution by Alkali and Hydrogen Peroxide Treatment 3 g of hair was added to 10 ml of a 1:1 mixed solution of hydrogen peroxide (6%) and ammonia (1.68%), the complex hyaluronic acid was added at test concentrations of 0.02, 0.01, and 0.005 weight %, respectively, and then a treatment was performed at room temperature for 30 minutes. 0.5 ml of the reaction solution was concentrated by using a Rapid-Con protein concentration kit (Elpis Biotech), the concentrated solution was electrophoresed in a 10% SDS-polyacrylamide gel by the method of Laemmli, and then the keratin protein in the gel was dyed for one hour with a mixed solution of 0.1% of Coomassie brilliant blue R 250, 10% of glacial acetic acid, and 40% of ethanol and was bleached in a mixed solution of 10% of glacial acetic acid and 40% of ethanol, to check a keratin protein band. A keratin band seen when only 50 μg of human hair keratin protein was electrophoresed by using ImageMaster software (Amersham Pharmacia Biotech) was set to 100%, comparison was performed with the group without the complex hyaluronic acid treatment as a control, and a keratin bonding effect was shown in Table 15 below in terms of %.

TABLE 15

| | Example 1 | | | |
|---|---|---|---|---|
| | Control | 0.02% | 0.01% | 0.005% |
| Hair elution keratin protein | 100% | 78% | 87% | 97% |

As shown in Table 15, it can be understood that as the complex hyaluronic acid content increased, the keratin protein content eluted from the hair decreased.

Experiment Example 16: Effect of Complex Hyaluronic Acid on Hair Tensile Strength and Elongation by Alkali and Hydrogen Peroxide Treatment 3 g of hair was added to 10 ml of a 1:1 mixed solution of hydrogen peroxide (6%) and ammonia (1.68%), the complex hyaluronic acid was added at test concentrations of 0.02, 0.01, and 0.005 weight %, respectively, a treatment was performed at room temperature for 30 minutes, the resultant was washed with water and dried with wind, and tensile strength (gf) and elongation (%) were measured on an Autograph tester. Table 16 shows the tensile strength and the elongation of the hair treated in this manner.

TABLE 16

| | Example 1 | | | |
|---|---|---|---|---|
| | Purified Water | 0.02% | 0.01% | 0.005% |
| Tensile strength (gf) | 113 | 121 | 116 | 113 |
| Elongation (%) | 45 | 49.1 | 47.7 | 44.5 |

As shown in Table 16, it can be understood that, when a treatment with a bleaching agent was performed for 30 minutes, as the amount of the complex hyaluronic acid, increased, the decrease in strength of the hair was suppressed. Accordingly, it is thought that, when the bleach treatment is performed, the hair protection effect by the complex hyaluronic acid can be expected.

Experimental Example 17: Production of Example 2 and Comparative Experiment of Skin Elasticity Improvement Effect and Wrinkle Improvement Effect Example 2 was produced as a cosmetic containing the complex hyaluronic acid obtained in Example 1, and a skin elasticity improvement effect and a wrinkle improvement effect on humans were evaluated in comparative experiments with Comparative Example 1.

The cosmetics used in the comparative experiments were in the form of creams, and the composition thereof is as shown in Table 17. First, a B) phase shown in Table 17 was heated and preserved at 0° C. An A) phase was added thereto, preliminary emulsification was performed, uniform emulsification was performed with a homogenizer, and then the emulsion was slowly cooled down to prepare a cream (Example 2, Comparative Example 1). For 20 subjects (20-35 year old female), the cream prepared in Example 2 was applied to the right side of the face, and the cream prepared in Comparative Example 1 was applied to the left side of the face twice a day for 2 consecutive months.

TABLE 17

| | Raw Material | Example 2 | Comparative Example 1 |
|---|---|---|---|
| A | Stearyl alcohol | 8 | 8 |
| | Stearic acid | 2 | 2 |
| | Stearic acid cholesterol | 2 | 2 |
| | Squalane | 4 | 4 |
| | 2-Octyldodecyl alcohol | 6 | 6 |
| | Polyoxyethylene (25 moles added) alcohol ester | 3 | 3 |
| | Glyceryl monostearic acid | 2 | 2 |
| B | Example 1 | 1 | — |
| | Propylene glycol | 5 | 5 |
| | Appropriate amount | Appropriate amount | Appropriate amount |

<Unit: weight %>

After the experiment was completed, the skin elasticity improvement effect was measured by using a skin elasticity measuring instrument (cutometer SEM 575, C+K Electronic Co., Germany) before using the product and after using the product for two months. Experimental results are shown in Table 18 in values of AR7 of Cutometer SEM 575, and the R7 values represents the nature of the viscoelasticity of the skin.

TABLE 18

| Experimental product | Skin elasticity effect (ΔR7) | Remark |
|---|---|---|
| Example 2 | 0.36 | |
| Comparative Example 1 | 0.12 | | n = 20,
p < 0.05

As shown in Table 18, it can be understood that the skin elasticity improvement effect of the subjects to which the cream including the complex hyaluronic acid was applied was excellent.

Further, for 20 subjects (20-35-year-old female), the cream prepared in Example 2 was applied to the right side of the face, and the cream prepared in Comparative Example 1 was applied to the left side of the face twice a day for 2 consecutive months.

After the experiment was completed, with respect to the skin wrinkle improvement effect, in order to search the wrinkle improvement effect before using the product and after using the product for two months, a silicone replica was produced, and a state of a wrinkle at a predetermined part was measured by using a visiometer (SV60, C+K Electronic Co., Germany).

The results are shown in Table 19. This represents averages of values obtained by subtracting each of parameter values before two months from each of parameter values after two months. That is, as the value is more negative, the wrinkle improvement effect is higher.

TABLE 19

| | Experimental product | | | | |
|---|---|---|---|---|---|
| | R1 | R2 | R3 | R4 | R5 |
| Example 2 | −0.25 | −0.22 | −0.11 | −0.07 | −0.06 |
| Comparative Example 1 | −0.12 | −0.08 | −0.05 | −0.04 | −0.02 |

R1: Difference between the highest and lowest wrinkle contours
R2: Average of R1 values after randomly dividing the wrinkle contours into 5 spaces
R3: Highest value of R1 values divided by into 5 spaces
R4: Average of values obtained by subtracting values of each top and valley in baseline of wrinkle contours
R5: Average of values obtained by subtracting values of each wrinkle outline in baseline of wrinkle contours As shown in Table 19, it can be understood that the skin wrinkle improvement effect of Example 2 containing the complex hyaluronic acid was greatly enhanced.

Experimental Example 18: Production of Example 3 and Comparative Experiment of Atopic Dermatitis Improvement Effect of Example 3

Example 3 was produced as a cosmetic containing the complex hyaluronic acid obtained in Example 1, and an atopic dermatitis improvement effect on humans was evaluated in comparative experiments with Comparative Example 2.

The cosmetics used in the comparative experiments were in the form of creams, and the composition thereof is as shown in Table 20. First, a B) phase shown in Table 20 was heated and preserved at 0° C. An A) phase was added thereto, preliminary emulsification was performed, uniform emulsification was performed with a homogenizer, and then the emulsion was slowly cooled down to prepare a cream (Example 3, Comparative Example 2).

TABLE 20

| | Raw Material | Example 3 | Comparative Example 2 |
|---|---|---|---|
| A | Stearyl alcohol | 8 | 8 |
| | Stearic acid | 2 | 2 |
| | Stearic acid cholesterol | 2 | 2 |
| | Squalane | 4 | 4 |
| | 2-Octyldodecyl alcohol | 6 | 6 |
| | Polyoxyethylene (25 moles added) alcohol ester | 3 | 3 |
| | Glyceryl monostearic acid | 2 | 2 |
| B | Example 1 | 1 | — |
| | Propylene glycol | 5 | 5 |
| | Appropriate amount | Appropriate amount | Appropriate amount |

In order to atopic skin improvement effect, the clinical experiment was conducted as follows. For thirty 5-30-year-old patients with atopic dermatitis and suffered from atopic dermatitis for more than two years, the atopic dermatitis improvement was examined. To the same person, the cream of Example 3 on the left hand and the cream of Comparative Example 2 on the right hand were applied to the skin once a day for 60 days after washing every evening, and the degree of atopic dermatitis improvement was measured. The measurement was performed by sensory evaluation by survey. The results thereof are shown in Table 21 below.

TABLE 21

| | Very good | Good | Ordinary |
|---|---|---|---|
| Example 3 | 70% (21 people) | 30% (9 people) | — |
| Comparative Example 2 | 10% (3 people) | 20% (6 people) | 70% (21 people) |

As shown in Table 21, it can be understood that the creme of Example 3 produced by adding the complex hyaluronic acid had more excellent atopic skin improvement effect than the cosmetic of the comparative formulation without adding the complex hyaluronic acid.

Experimental Example 19: Experiment on Effect of Relieving Skin Irritation Caused by SLS In this experiment example, the stimulation relieving effect of a cosmetics containing the complex hyaluronic acid obtained in Example 1 was evaluated by a human patch experiment.

1% of SLS (sodium lauryl sulfate) that causes stimulation in general cosmetic prescription (cream, lotion, skin, or essence) and the product produced in Example 3 were mixed and patched for 24 hours, 48 hours, and 72 hours, and the stimulus relieving effect was evaluated based on a stimulus inducing index.

0.3 mg of each product was patched on the upper arms of fifty 20-50-year-old healthy men and women by using FINN CHAMBER (FINLAND), and after 24 hours, an acute stimulation index was evaluated. After the evaluation, the same amount of product was patched on the same parts, and after 48 and 72 hours, the delayed stimulus index was evaluated.

As results of the experiments, red stimulation appeared on the SLS-only patched parts after 24 hours, but the product containing the complex hyaluronic acid did not cause skin seizures after 24 hours, 48 hours, or 72 hours from the patching.

The results of this evaluation indicate that the complex hyaluronic acid, when being mixed in cosmetics, has a significant effect on reducing skin irritation by substrates (surfactants, fragrances, or alcohol) that induce stimulation.

Other examples are shown below. That is, a toner, an emulsion, and a cosmetic solution containing the complex hyaluronic acid obtained in Example 1 were prepared in Examples 4 to 6. A toner, an emulsion, and a cosmetic solution that contain hyaluronic acid exhibit excellent effects on skin improvement such as an antioxidizing effect, a collagen synthesis promoting effect, a skin fine wrinkle improvement effect, a moisturizing effect, a skin irritation relief effect, an acne prevention effect, an atopy improvement effect, and an anti-inflammatory effect, an hair damage prevention effect, and a hair loss prevention and hair growth effect.

Example 4: Production of Toner Containing Complex Hyaluronic Acid Obtained in Example 1

0.05 g of polypyrrolidone, 0.1 g of oleyl alcohol, 0.2 g of polyoxyethylene monooleate, 0.2 g of fragrance, 0.1 g of paraoxybenzoate methyl ester, and a small amount of antioxidant, and a small amount of pigment were mixed with and dissolved in 8 g of 95% of ethanol. 0.05 g of the complex hyaluronic acid obtained in Example 1 and 5 g of glycerin were dissolved in 85.33 g of purified water, and the mixed solution was added and stirred to obtain a toner having an effect of improving skin.

Example 5: Production of Emulsion Containing Complex Hyaluronic Acid Obtained in Example 1

1.2 g of cetyl alcohol, 10 g of squalane, 2 g of vaseline, 0.2 g of paraoxybenzoic acid ethyl ester, 1 g of glycerin monostearate, 1 g of polyoxyethylene (20 mole added) monooleate, and 0.1 g of fragrance were heated, mixed, and dissolved at 70° C. 0.5 g of the complex hyaluronic acid obtained in Example 1, 5 g of dipropylene glycol, 2 g of polyethylene glycol-1500, 0.2 g of triethanolamine, and 76.2 g of purified water were heated and dissolved at 75° C. Both were mixed and emulsified and cooled to obtain an oil-in-water (O/W)-type emulsion having a skin improvement effect.

Example 6: Production of Cosmetic Solution Containing Complex Hyaluronic Acid Obtained in Example 1

1.2 g of polyoxyethylene sorbitan monooleate, 0.3 g of chitulose, 0.2 g of sodium hyaluronate, 0.2 g of vitamin E-acetate, 0.2 g of sodium licorice, 0.1 g of paraoxybenzoic acid ethyl ester, 1 g of the complex hyaluronic acid obtained in Example 1, and an appropriate amount of pigment were mixed with 5 g of 95% ethyl alcohol to obtain a cosmetic solution having a skin improvement effect.

Experimental Example 20: Production of Example 7 and Experiment on Mosquito Repellent Effect 0.05 g of polypyrrolidone, 0.1 g of oleyl alcohol, 0.2 g of polyoxyethylene monooleate, 0.2 g of fragrance, 0.1 g of paraoxybenzoate methyl ester, and a small amount of antioxidant, and a small amount of pigment were mixed with and dissolved in 8 g of 95% of ethanol. 0.05 g of the complex hyaluronic acid obtained in Example 1, 0.03 g of fermentation broth of pink pampas, and 5 g of glycerin were dissolved in 85.33 g of purified water, and the mixed solution was added thereto and stirred to obtain a toner having a mosquito repellent effect.

Pink pampas is poaceae called pink mulley, western pampas, or the like, and the scientific name thereof is *Muhlenbergia capillaris*.

The home of pink pampas is known to be warm plains of the western and central United States, and pink pampas is widely planted for landscaping, domestically in Jeju Island, Gyeongju, or the like.

There have been no reported cases of using pink pampas as a raw material of a toner.

As the fermentation broth of pink pampas, one obtained by collecting leaves of pink pampas, mixing the leaves of pink pampas, salt, and vinegar in the ratio of 1:1:2, performing fermentation for 15 days, and obtaining a supernatant obtained by separating solids was used.

In addition, the mosquito repellent effect was experimented by using the toners of Examples 4 and 7.

The samples of Example 4 and Example 7 were evenly applied to parts between fingers and elbows of healthy adults who voluntarily participated in the experiment, and then naturally dried for two minutes.

The arms of the subjects to which the samples were applied and the arms without application were simultaneously introduced into a 50×50×50 $cm^3$ bioassay cage which is housed by 100 female red mosquitos, covered with a mesh, and the number of mosquitoes sucking the arm for three hours at intervals of 30 minutes was recorded. Results thereof are shown in Table 22 below.

TABLE 22

| | Number of sucking mosquitoes | | | | | |
|---|---|---|---|---|---|---|
| Category | 30 minutes elapsed | 60 minutes elapsed | 90 minutes elapsed | 120 minutes elapsed | 150 minutes elapsed | 180 minutes elapsed |
| Example 4 | 8 | 8 | 7 | 9 | 10 | 11 |
| Example 7 | 0 | 0 | 0 | 1 | 2 | 3 |

As shown in Table 22, it can be understood that the arms of the subjects to which the toner of Example 7 is applied exhibited excellent mosquito repellent effect overall.

As described above, the complex hyaluronic acid according to the present invention exhibits excellent anti-aging effects such as an active oxygen scavenging effect, an MMP inhibitory effect, an MMP expression control effect by UV irradiation, and a skin fine wrinkle improvement effect, and an effect of relieving skin irritation caused after UV irradiation.

In addition, the complex hyaluronic acid according to the present invention exhibits a skin irritation relief effect and an atopy improvement effect by the inflammatory mediator.

In addition, the complex hyaluronic acid according to the present invention exhibits excellent hair damage and hair loss prevention effects, an antibiotic activity effect of acne bacteria having an acne prevention effect and an effect of inhibiting 5-alpha-reductase.

Accordingly, it can be found that the cosmetic compositions such as lotions, creams, latex, packs, powders etc. containing the complex hyaluronic acid have skin preparation effects for external use such as an active oxygen scavenging effect, a collagen degrading enzyme activity modulating effect, a skin wrinkle improvement effect, a moisturizing effect, a skin irritation relief effect, an acne prevention effect, an atopy improvement effect, and an anti-inflammatory effect, an hair damage prevention effect, and a hair loss prevention and hair growth effect.

While the present invention has been described with respect to the specific embodiments, it will be apparent to those skilled in the art that various changes and modifications may be made without departing from the spirit and scope of the invention as defined in the following claims.

What is claimed is:

1. A skin preparation composition for external use consisting of complex hyaluronic acid and purified water,
    wherein the complex hyaluronic acid consisting of hyaluronic acid, sodium hyaluronate, and hydrolyzed hyaluronic acid is contained by 0.001 to 3 weight % with respect to the total composition.

2. The skin preparation composition for external use containing complex hyaluronic acid according to claim 1,
    wherein the skin preparation composition for external use has an anti-aging effect.

3. The skin preparation composition for external use containing complex hyaluronic acid according to claim 1,
    wherein the skin preparation composition for external use has an irritation relief function.

4. The skin preparation composition for external use containing complex hyaluronic acid according to claim 1,
    wherein the skin preparation composition for external use has an atopic skin improvement function.

* * * * *